(12) United States Patent
Lawrence (10) Patent No.: US 10,238,436 B2
(45) Date of Patent: Mar. 26, 2019

(54) TEMPORARY FRACTURE STABILIZATION DEVICE

(71) Applicant: University of Kentucky Research Foundation, Lexington, KY (US)

(72) Inventor: Steven J. Lawrence, Lancaster, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 497 days.

(21) Appl. No.: 14/279,886

(22) Filed: May 16, 2014

(65) Prior Publication Data

US 2015/0327892 A1 Nov. 19, 2015

(51) Int. Cl.
*A61B 17/72* (2006.01)

(52) U.S. Cl.
CPC .................. *A61B 17/72* (2013.01)

(58) Field of Classification Search
CPC .............. A61B 17/72; A61B 17/68; A61B 17/7208–17/7241; A61B 2017/565; Y10T 403/75; Y10T 403/7062; Y10T 403/5733; Y10T 403/5741; Y10T 403/5746; Y10T 403/4674
USPC ..................................... 606/62–64
See application file for complete search history.

(56) References Cited

U.S. PATENT DOCUMENTS

| | | | |
|---|---|---|---|
| 2,672,861 A | 3/1954 | Jonas et al. | |
| 3,979,779 A | 9/1976 | Zeibig et al. | |
| 4,190,044 A | 2/1980 | Wood | |
| 4,467,794 A | 8/1984 | Maffei et al. | |
| 4,805,607 A | 2/1989 | Engelhardt et al. | |
| 4,938,768 A | 7/1990 | Wu | |
| 5,433,718 A * | 7/1995 | Brinker | A61B 17/72 606/62 |
| 6,019,794 A * | 2/2000 | Walker | A61F 2/385 623/20.22 |
| 6,569,203 B1 | 5/2003 | Keller | |
| 7,125,423 B2 | 10/2006 | Hazebrouck | |
| 7,141,067 B2 | 11/2006 | Jones et al. | |
| 8,696,668 B2 | 4/2014 | Winquist et al. | |
| 2003/0073999 A1* | 4/2003 | Putnam | A61B 17/7291 606/62 |
| 2004/0193267 A1* | 9/2004 | Jones | A61F 2/28 623/16.11 |
| 2004/0193268 A1* | 9/2004 | Hazebrouck | A61F 2/28 623/16.11 |
| 2005/0277926 A1* | 12/2005 | Farris | A61B 17/7014 606/260 |
| 2006/0149246 A1* | 7/2006 | Jones | A61F 2/28 606/62 |
| 2006/0195096 A1* | 8/2006 | Lee | A61B 17/7037 606/278 |

(Continued)

FOREIGN PATENT DOCUMENTS

DE 3528728 A1 2/1987
DE 19722389 A1 12/1998

*Primary Examiner* — Ellen C Hammond
*Assistant Examiner* — Tessa M Matthews
(74) *Attorney, Agent, or Firm* — King & Schickli, PLLC (57) ABSTRACT

A temporary fracture stabilization device includes a first intramedullary fixation rod, a second intramedullary fixation rod, a first extramedullary connector, a second extramedullary connector and a fastener. A field kit for temporary fracture stabilization is also disclosed.

30 Claims, 6 Drawing Sheets

(56) References Cited

U.S. PATENT DOCUMENTS

| | | | |
|---|---|---|---|
| 2009/0198342 A1* | 8/2009 | Parsell | A61B 17/68 623/23.48 |
| 2010/0137862 A1* | 6/2010 | Diao | A61B 17/68 606/62 |
| 2010/0318085 A1 | 12/2010 | Austin et al. | |
| 2012/0022533 A1* | 1/2012 | Buettler | A61B 17/1725 606/62 |
| 2012/0209265 A1* | 8/2012 | Pool | A61B 17/7216 606/55 |
| 2012/0259419 A1* | 10/2012 | Brown | A61F 2/4225 623/21.19 |
| 2015/0018828 A1* | 1/2015 | Dorris | A61B 17/72 606/62 |

\* cited by examiner

TEMPORARY FRACTURE STABILIZATION DEVICE

TECHNICAL FIELD

This document relates generally to external bone fixation or stabilization devices and more particularly to a temporary device for retaining and holding broken and/or fractured bones in a desired configuration until they can be permanently set such as by means of a traditional intramedullary rod.

BACKGROUND

Intramedullary rods, such as disclosed in U.S. Pat. No. 4,467,794 to Maffei et al. are metal implants used to stabilize long bone fractures. The rods are placed into the center of the bone in the medullary canal and left in place after the fracture heals.

With severe compound or open fractures, such metal implants or rods are not inserted until the chance of infection is passed. Instead, the bone and soft tissue envelope are cleaned by "debridement and washing" to decrease bacterial count and to remove contaminated devascularized tissue. Temporary stability is provided to the limb by means of an external fixator device applied to the bone. One such device is disclosed in, for example, U.S. Pat. No. 8,696,668 to Winquist et al.

This document relates to a new and improved temporary fracture stabilization device. The device provides temporary fracture stabilization until conditions are appropriate for permanent repair with a traditional intramedullary rod. Unlike prior art temporary fracture stabilization devices or frames, the new temporary stabilization device incorporates two intramedullary fixation rods that are connected together by means of two extramedullary connectors and a fastener that extend outside the bone canal and allow for timely disassembly and implant retrieval. The temporary fracture stabilization device is unique as the construct provides temporary fracture stability and time released antibiotic treatment. The device incorporates a relatively simple structure that may be quickly and relatively easily utilized to stabilize an open fracture. As such it is particularly useful in the field including, particularly, by field medics on battlefields.

SUMMARY

In accordance with the purposes and benefits described herein, a temporary fracture stabilization device comprises a first intramedullary fixation rod having a first extramedullary connector, a second intramedullary fixation rod having a second extramedullary connector and a fastener securing the first extramedullary connector to the second extramedullary connector. In one possible embodiment the fastener comprises at least one screw that engages both of the connectors. In one possible embodiment the first extramedullary connector is a first plate and the second extramedullary connector is a second plate. The first plate includes a first face and the second plate includes a second face with the first and second faces engaging together when the first and second fixation rods are fastened together. In one embodiment the faces include a series of cooperating serrations so that when the plates are engaged, the serrations interdigitate to prevent the first fixation rod from twisting with respect to the second fixation rod when the fastener screw is tightened in place.

The first and second intramedullary fixation rods are made from any appropriate material including, but not necessarily limited to, a metal, titanium, stainless steel, a plastic, polymethylmethacrylate, polyethylene, polypropylene, polyethylene terephthalate, polyester, polyamide, nylon, polytetrafluoroethylene and mixtures thereof. Where the rods are made of a polymer or a composite such as polymethylmethacrylate they may incorporate an antibiotic for time release into the bone adjacent the fracture. That antibiotic may be selected from a group consisting of tobramycin, cefazalin, vancomycin and mixtures thereof.

The first and second intramedullary fixation rods generally have a diameter of between about 3.0 mm and about 12.0 mm and a length of between about 4.0 cm and about 12.0 cm. The first and second plates, which are typically made from a metal such as stainless steel or titanium, generally have a length of between about 10.0 mm and about 16.0 mm, a width of between about 10.0 mm and about 16.0 mm and a thickness of between about 1.0 mm and about 2.0 mm. Further each of the rods may include a beveled distal end to aid in insertion into the intramedullary cavity.

In accordance with an additional aspect, a temporary fracture stabilization field kit is provided. The field kit comprises a plurality of intramedullary fixation rods, a first extramedullary connector, a second extramedullary connector, a fastener to secure the first and second extramedullary connectors together and a screw driver. In one possible embodiment the kit further includes a hand broach which may be used to prepare the medullary canal of a fractured bone for receipt of one of the intramedullary fixation rods.

In one possible embodiment the kit further includes a container for holding the other components of the kit. Further, in one embodiment the kit may include an instruction sheet describing the components of the kit and their use. In any of the embodiments the plurality of intramedullary rods provided with the kit will include rods of different lengths and diameters. The medic or other individual utilizing the kit to temporarily stabilize an open fracture will select the two rods of best length and diameter to complete the procedure.

In the following description, there are shown and described several preferred embodiments of the temporary fracture stabilization device. As it should be realized, the device is capable of other, different embodiments and its several details are capable of modification in various, obvious aspects all without departing from the device as set forth and described in the following claims. Accordingly, the drawings and descriptions should be regarded as illustrative in nature and not as restrictive.

BRIEF DESCRIPTION OF THE DRAWINGS

The accompanying drawings incorporated herein and forming a part of the specification, illustrate several aspects of the temporary fracture stabilization device and together with the description serve to explain certain principles thereof. In the drawings.

Reference will now be made in detail to the present preferred embodiments of the temporary fracture stabilization device, examples of which are illustrated in the accompanying drawings.

DETAILED DESCRIPTION

Figure 1:
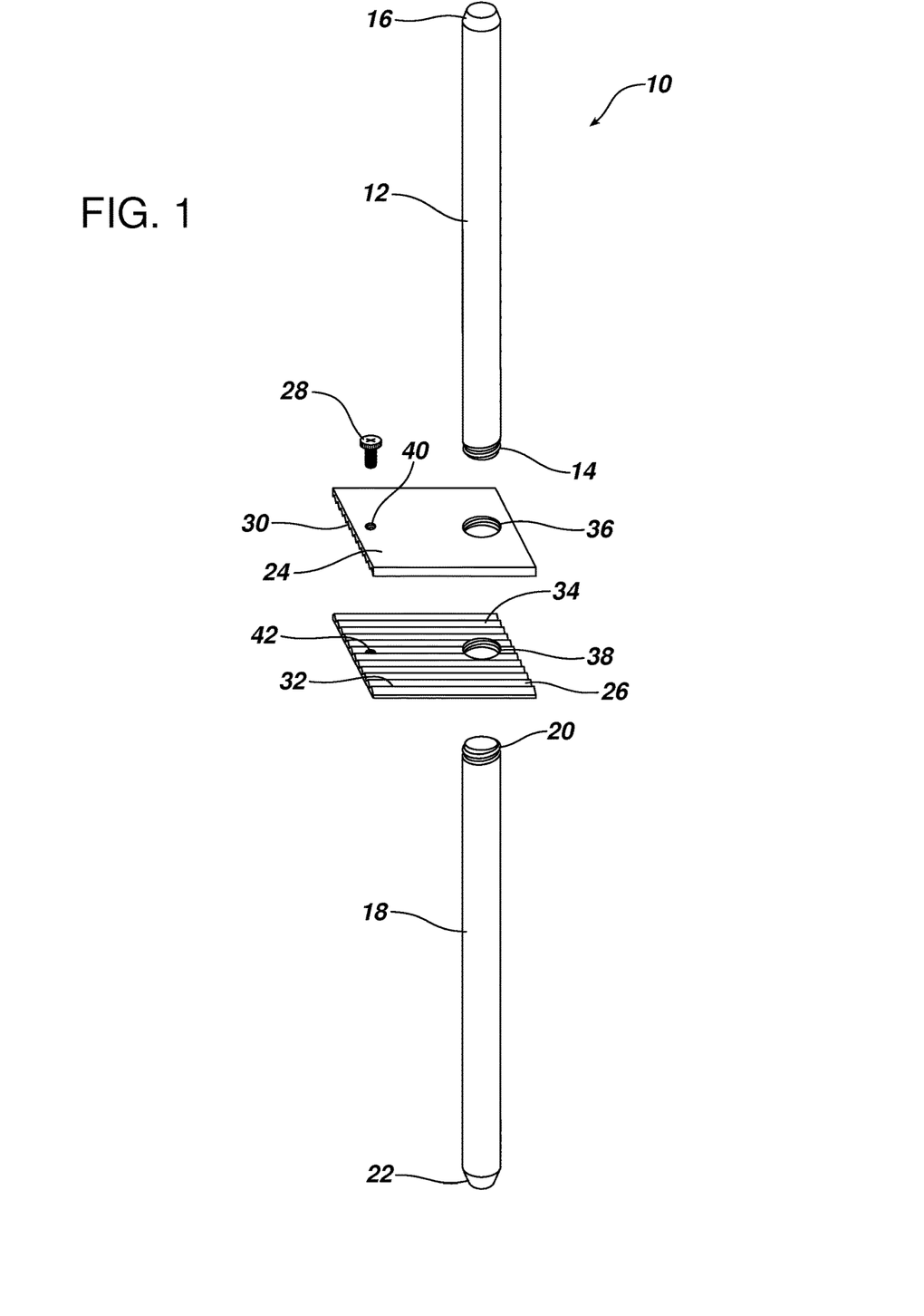
FIG. 1 is an exploded perspective view of the temporary fracture stabilization device.
Figure 2:
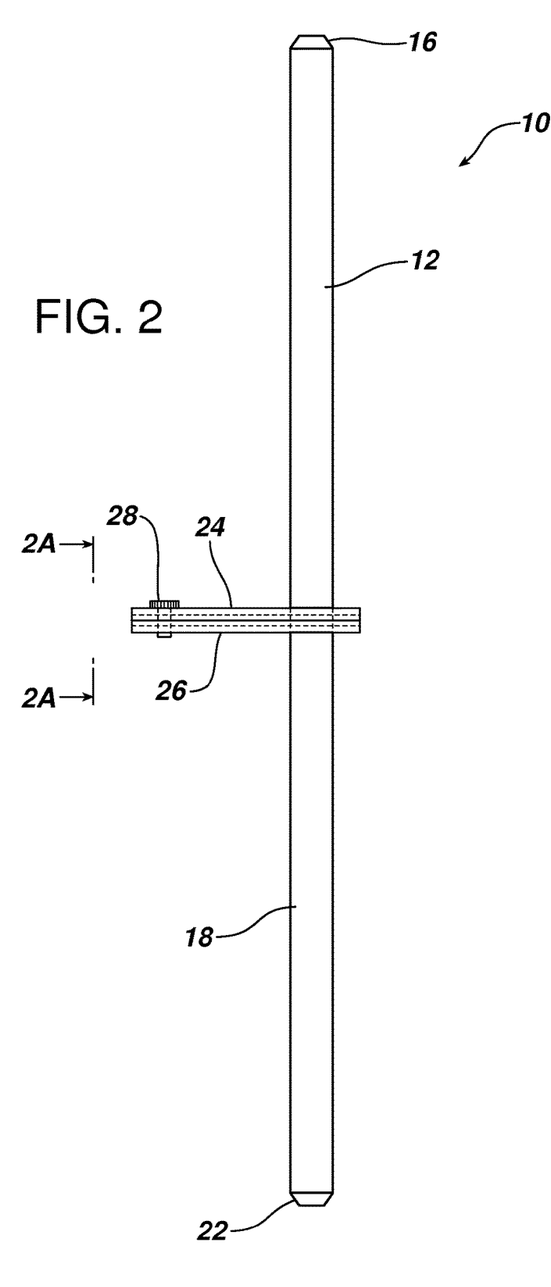
FIG. 2 is a front elevational view showing the assembled device in position to stabilize a fracture.

Reference is now made to FIGS. 1 and 2 illustrating the temporary fracture stabilization device 10. That device 10 includes a first intramedullary rod 12, having a threaded proximal end 14 and a beveled distal end 16, and a second intramedullary rod 18, having a threaded proximal end 20 and a beveled distal end 22. In one possible embodiment the first and second rods 12, 18 have a diameter of between about 3.0 mm and about 12.0 mm and a length of between about 4.0 cm and about 12.0 cm. In one embodiment the rods 12, 18 are made from a metal approved by the FDA for implantation including, for example, titanium and stainless steel. In another embodiment the rods 12, 18 are made from a plastic approved by the FDA for implantation including, but not necessarily limited to, polymethylmethacrylate, polyethylene, polypropylene, polyethylene terephthalate, polyester, polyamide, nylon, polytetrafluoroethylene and mixtures thereof. That plastic may be a composite material incorporating plastic reinforced with fibers or other appropriate materials such as carbon nanotubes.

Figure 2A:
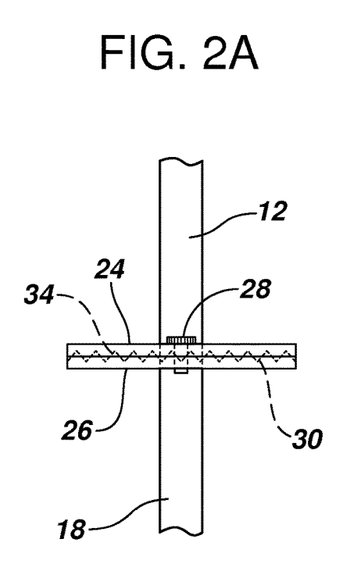
FIG. 2a is a detailed view of the meshing connectors of FIG. 2 reoriented 90° to show the interdigitating serrations.

As further illustrated in FIGS. 1 and 2, the stabilization device 10 also includes a first extramedullary connector 24, a second extramedullary connector 26 and a fastener 28 for securing the two connectors together. In the illustrated embodiment the first extramedullary connector 24 comprises a first plate while the second extramedullary connector 26 comprises a second plate. In one possible embodiment each connector/plate 24, 26 has a length about 10.0 mm and about 16.0 mm, a width of between about 10.0 mm and about 16.0 mm and a thickness of between about 1.0 mm and about 2.0 mm. The connector/plates 24, 26 also include cooperating engagement faces 30, 32 that engage together when the first and second fixation rods 12, 18 are connected together. In the illustrated embodiment the faces 30, 32 include cooperating serrations 34 which interdigitate when the plates are engaged to prevent relative twisting of the connectors 24, 26 and rods 12, 18 with respect to each other when held together by means of the fastener 28 (see also FIG. 2a).

In the illustrated embodiment, the threaded proximal end 14 of the first intramedullary fixation rod 12 is secured in a threaded aperture 36 in the first connector 24. Similarly the threaded proximal end 20 of the second intramedullary fixation rod 18 is secured in the threaded aperture 38 in the second plate or connector 26. The integrity of the threaded connection may be enhanced by providing an appropriate adhesive between the threads on the proximal ends 14, 20 of the rods 12, 18 and the apertures 36, 38 in the connectors 24, 26.

In one possible embodiment the connectors 24, 26 are made from an appropriate FDA approved implantation metal such as stainless steel or titanium. In one possible embodiment the rods 12, 18 connected to the connectors 24, 26 are made from polymethylmethacrylate composite material incorporating an antibiotic for time release into the bone adjacent the fracture. That antibiotic may be any appropriate antibiotic suitable for this purpose including, but not necessarily limited to tobramycin, cefazalin, vancomycin and mixtures thereof.

Typically, the fastener or screw 28 utilized to secure the plates or connectors 24, 26 together is also made from metal such as titanium or stainless steel. That screw may also be coated with an adhesive before tightening in the aligned threaded apertures 40, 42 in the two plates 24, 26 in order to improve the integrity of the connection.

Figure 3:
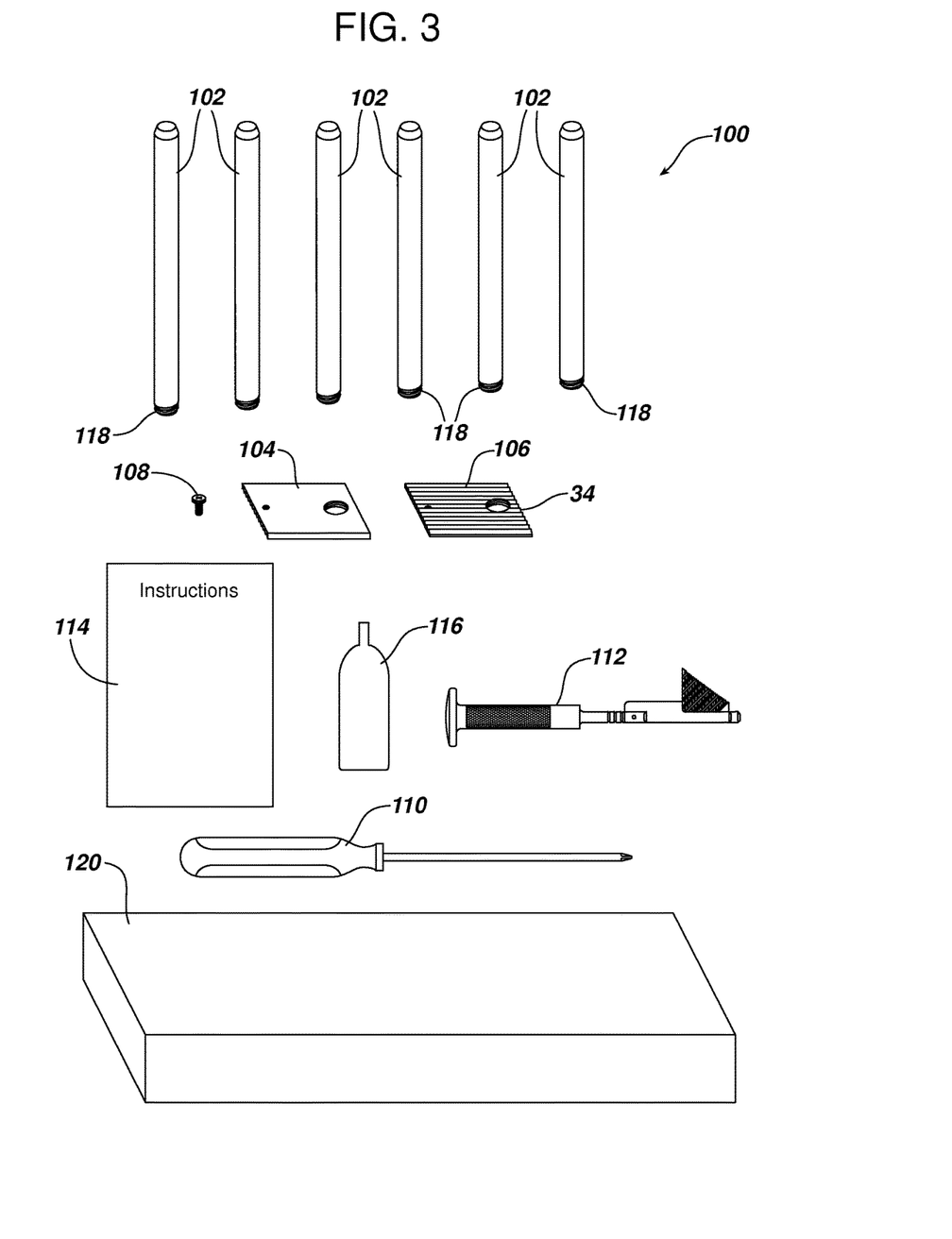
FIG. 3 illustrates a temporary fracture stabilization field kit incorporating the device illustrated in FIGS. 1, 2.

Reference is now made to FIG. 3 illustrating a temporary fracture stabilization field kit 100. The field kit 100 comprises a plurality of intramedullary fixation rods 102, a first extramedullary connector 104, a second extramedullary connector 106 and a fastener 108 that is used to secure the first and second extramedullary connectors together. In the illustrated embodiment the kit further includes a screw driver 110 and a hand broach 112. The screw driver 110 is utilized to tighten the fastener 108 in order to secure the first and second connectors 104, 106 together. The hand broach 112 is utilized when required to prepare either or both ends of the medullary canal of the fractured bone for receipt of the fixation rods 102.

As should further be appreciated, the illustrated kit 100 also includes an instruction sheet 114, which provides information about the kit components and their use in stabilizing an open fracture, and a tube of adhesive 116. As described above, the adhesive 116 may be applied to the threaded distal ends 118 of the rods 102 to be used in the procedure so that those rods may be better secured in the connectors 104, 106. Further, the adhesive may be applied to the fastener 108 to help secure the fastener in the connectors 104, 106 and hold the entire assembly together. A container 120 made of soft vinyl, hard plastic or other appropriate material holds all of the components of the kit 100 as described above.

As illustrated, the kit 100 includes six intramedullary fixation rods. It should be appreciated that the kit may include any multiple of rods from 2-20 or more. As illustrated the kit 100 includes two connectors 104, 106 as two connectors are required to complete the device used in the medical procedure. It should be appreciated that the kit 100 could include more connectors 104, 106 so that it could be used for multiple procedures. Similarly the kit 100 includes a single fastener 108 as a single fastener is required to complete the assembly of the device 10. It should be appreciated that other embodiments of the kit could also include multiple fasteners 108.

Figure 4A:
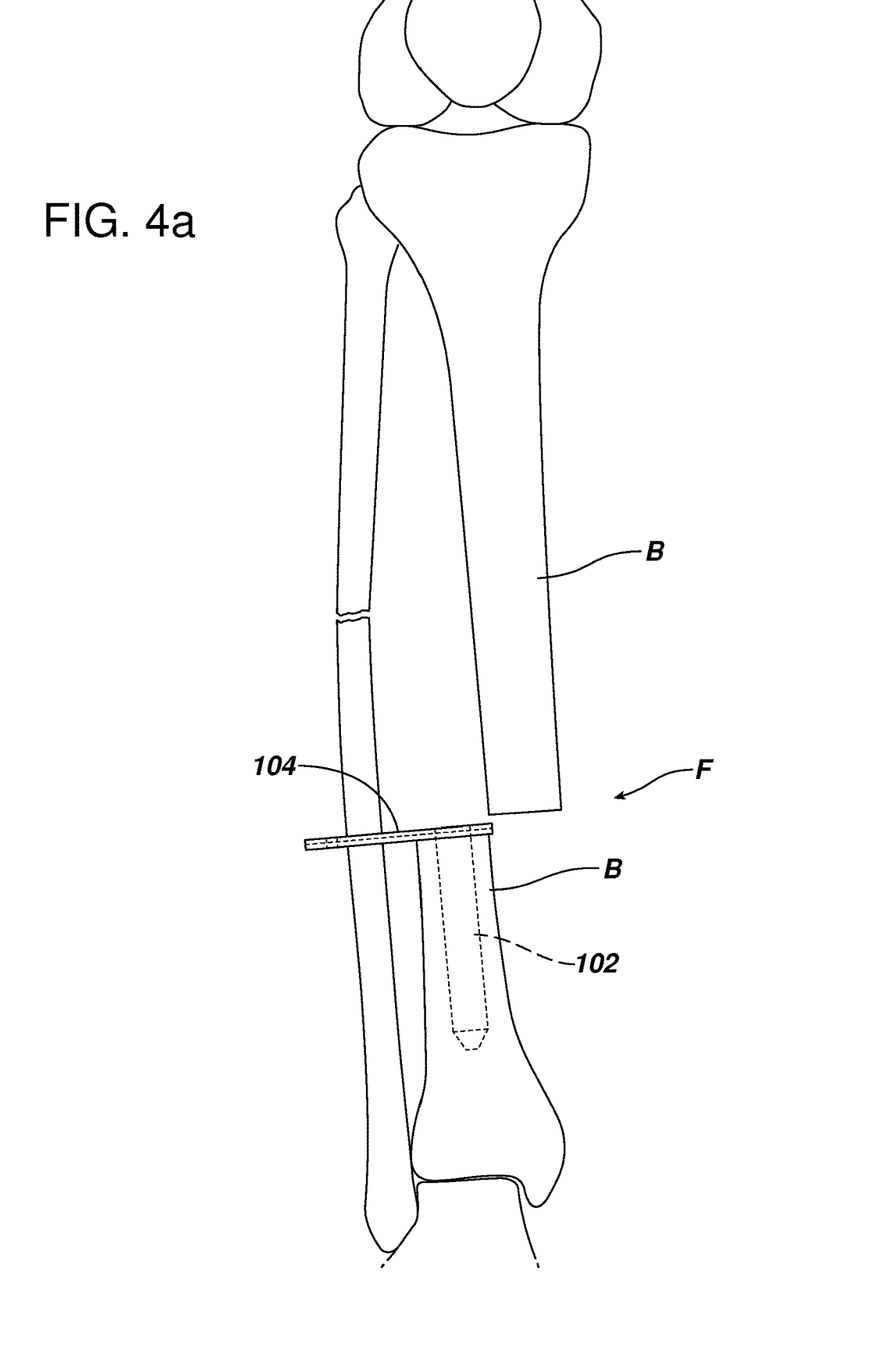
FIGS. 4a-4c illustrate the method of stabilizing a fracture utilizing the temporary fracture stabilization device illustrated in FIGS. 1 and 2.
Figure 4B:
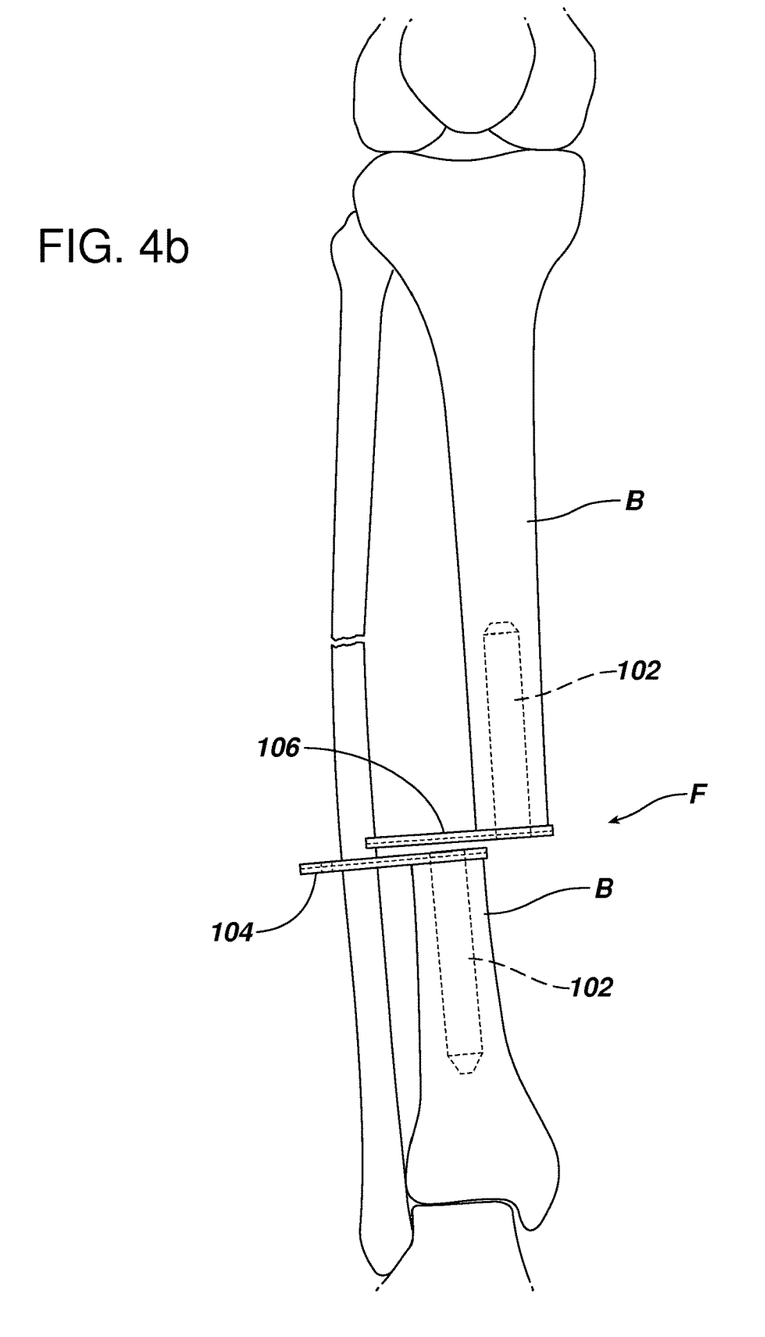
Figure 4C:
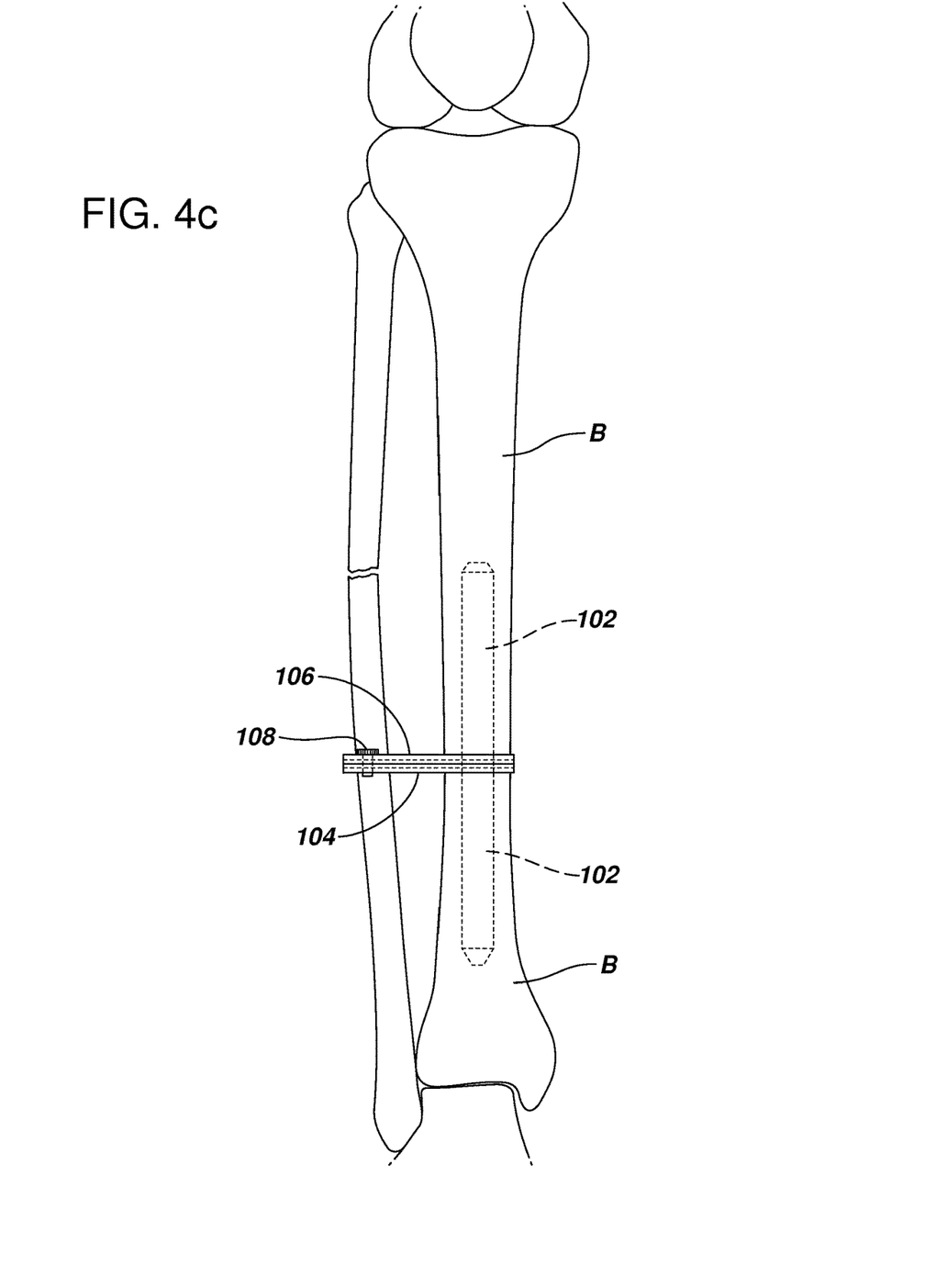

Reference is now made to FIGS. 4a-4c which helped illustrate the use of the temporary fracture stabilization device 10 found in the kit 100. The temporary fracture stabilization device 10 provides a quick, straight-forward and cost effective means to stabilize severe open limb fractures. Further in those embodiments incorporating antibiotic in the rods 12, 18, 102, a time release antibiotic is provided to the open wound. While useful for other purposes and other applications, the device 10 and kit 100 is particularly useful in the battlefield arena where prompt stabilization of high-energy ballistic injuries is frequently encountered.

After irrigation and debridement of the open fracture, the medic would select two hemi rods 102 of appropriate length and diameter for the stabilization procedure. These selected rods 102 would be attached to the connectors 104, 106 by means of the threaded ends 118. Optionally, the adhesive 116 could be applied to the threaded ends 118 prior to completing the connection if desired.

The selected rods 102 are then pushed into the exposed medullary canal in the bone B of the open fracture F (see FIGS. 4a and 4b). The hand broach 112 may be utilized to prepare the medullary canal for receipt of the rods 102 if necessary. Once the rods 102 are inserted, the fractured bone is aligned by bringing the plates 104, 106 together and the screw driver 110 is then used to tighten the fastener 108 to hold the plates together (see FIG. 4c). The interdigitated serrations 34 on the juxtaposed faces of the plates 104, 106 complete the secure connection which prevents any twisting. The injured soldier may then be transported to a facility with more advanced capabilities. During this transport, the device 10 would allow for the stabilization of the fracture and local delivery of antibiotics without use of external fixators and IV antibiotics.

Of course, the device 10 and kit 100 have applications beyond the battlefield. The device could be used in trauma centers or in other situations.

The foregoing has been presented for purposes of illustration and description. It is not intended to be exhaustive or to limit the embodiments to the precise form disclosed. Obvious modifications and variations are possible in light of the above teachings. For example, in the illustrated embodiments the rods 12, 18, 102 are connected to the plates 24, 26, 104, 106 by means of the threaded proximal ends. In other embodiments a friction fit could be used. In still others, the rods and plates could be cast as one piece. Similarly, other structures could be used to engage the plates together in place of the cooperating serrations. For example integral pins and cooperating apertures could be used. All such modifications and variations are within the scope of the appended claims when interpreted in accordance with the breadth to which they are fairly, legally and equitably entitled.

What is claimed:

1. A temporary fracture stabilization device for use in stabilizing a bone internal to a body of a patient, said bone including a medullary canal, the device comprising:
    a first intramedullary fixation rod;
    a second intramedullary fixation rod;
    a first extramedullary connector plate;
    a second extramedullary connector plate; and
    a fastener securing said first extramedullary connector plate to said second extramedullary connector plate at a position exterior to a path of the medullary canal of the bone and external to the body of the patient, wherein the first and second extramedullary connector plates are aligned to define a connector plate central axis through a center of both of the first extramedullary plate and the second extramedullary plate;
    wherein the first and second intramedullary fixation rods longitudinally align to form a fixation rod central axis through a longitudinal central axis of both the first and secondary intramedullary fixation rods; and
    wherein the connector plate central axis is parallel to but not aligned with the fixation rod central axis.

2. The device of claim 1, wherein said fastener comprises at least one screw that engages both said first and second extramedullary connector plates.

3. The device of claim 2, wherein said first extramedullary connector plate includes a first threaded aperture and said second extramedullary connector plate includes a second threaded aperture, said screw being received in said first and second threaded apertures in order to align said first and second intramedullary fixation rods together.

4. The device of claim 1, wherein said first and second intramedullary fixation rods are made from a material selected from a group consisting of a metal, titanium, stainless steel, a plastic, polymethylmethacrylate, polyethylene, polypropylene, polyethylene terephthalate, polyester, polyamide, nylon, polytetrafluoroethylene and mixtures thereof.

5. The device of claim 4, wherein said first and second extramedullary connector plates are made from metal.

6. The device of claim 5, wherein said metal is selected from a group of metals consisting of titanium and stainless steel.

7. The device of claim 1, wherein said first and second intramedullary fixation rods are made from polymethylmethacrylate composite material.

8. The device of claim 7, wherein said polymethylmethacrylate composite material incorporated an antibiotic for time release into bone adjacent the fracture.

9. The device of claim 8, wherein said antibiotic is selected from a group consisting of tobramycin, cefazalin, vancomycin and mixtures thereof.

10. The device of claim 8, wherein said first and second extramedullary connector plates are made from metal.

11. The device of claim 10, wherein said metal is selected from a group of metals consisting of titanium and stainless steel.

12. The device of claim 1, wherein said first extramedullary connector plate includes a first threaded aperture and said second extramedullary connector plate includes a second threaded aperture.

13. The device of claim 12, wherein said fastener is a screw that is received and engaged in said first and second threaded apertures in order to align said first and second intramedullary fixation rods and hold said first and second intramedullary fixation rods together.

14. The device of claim 1, wherein said first and second intramedullary fixation rods have a diameter of between about 3.0 mm and about 12.0 mm and a length of between about 4.0 cm and about 12.0 cm.

15. The device of claim 1, wherein said first and second extramedullary connector plates have a length of between about 10.0 mm and about 16.0 mm, a width of between about 10.0 mm and about 16.0 mm and a thickness of between about 1.0 mm and about 2.0 mm.

16. The device of claim 1, wherein said first and second intramedullary fixation rods each include a beveled distal end.

17. The device of claim 1, wherein said first extramedullary connector plate includes a first face and said second extramedullary connector plate includes a second face, said first and second faces engaging together when said first and second fixation rods are fastened together.

18. The device of claim 17, wherein said first face includes a first serration and said second face includes a second serration, said first and second serrations cooperating when engaged to prevent said first fixation rod from twisting with respect to said second fixation rod when said first and second fixation rods are fastened together.

19. The device of claim 1, wherein the fastener is adapted to align in a direction parallel to the fixation rod central axis.

20. The device of claim 1, wherein upon fixing the first extramedullary connector plate to the second extramedullary connector plate with the fastener and upon placement of the first intramedullary fixation rod and the second intramedullary fixation rod in the medullary canal, at least a portion of both the first extramedullary connector plate and the second extramedullary connector plate are adapted to be external to the body.

21. The device of claim 1, wherein the first and second extramedullary connector plates together form a planar body.

22. A temporary fracture stabilization field kit for use in stabilizing a bone inside a body of a patient, comprising:
- a plurality of intramedullary fixation rods;
- a first extramedullary connector plate;
- a second extramedullary connector plate;
- a fastener adapted to secure said first and second extramedullary connector plates together at a location external to a cross-section of the bone and external to the body of the patient; and
- a screw driver;
- wherein upon assembly, the plurality of intramedullary fixation rods are adapted to align to define a fixation rod central axis through a longitudinal central axis of at least two of the plurality of intramedullary fixation rods, the first and second extramedullary connector plates are adapted to align to define a connector plate central axis through a center of both of the first and second extramedullary connector plates, and wherein the fixation rod central axis is parallel to but does not align with the connector plate central axis.

23. The kit of claim 22, further including a hand broach.

24. The kit of claim 22, further including a container for holding said plurality of intramedullary fixation rods, said first and second extramedullary connector plates, said fastener and said screw driver.

25. The kit of claim 22, including an instruction sheet.

26. The kit of claim 22, wherein said plurality of intramedullary rods have different lengths and diameters.

27. The kit of claim 22, further including an adhesive.

28. The kit of claim 22, wherein the fastener is adapted to align in a direction parallel to the fixation rod central axis.

29. The kit of claim 22, wherein assembly comprises fixing the first extramedullary connector plate to the second extramedullary connector plate with the fastener and upon placement of a first intramedullary fixation rod and a second intramedullary fixation rod in the medullary canal, and wherein upon assembly at least a portion of both the first extramedullary connector plate and the second extramedullary connector plate are adapted to be external to the body.

30. The kit of claim 22, wherein upon assembly, the first and second extramedullary connector plates form a planar body.

* * * * *